United States Patent [19]

Hauser

[11] Patent Number: 5,599,317

[45] Date of Patent: Feb. 4, 1997

[54] EXTERNALIZED SEALED CATHETER WITH LEAKPROOF ACCESS

[76] Inventor: Jean-Luc Hauser, 1499 chemin S. Maymes, F-06600 Antibes, France

[21] Appl. No.: 562,625

[22] Filed: Nov. 24, 1995

Related U.S. Application Data

[63] Continuation of Ser. No. 170,206, filed as PCT/FR93/00412, Apr. 28, 1993 published as WO 93/21972, Nov. 11, 1993, abandoned.

[30] Foreign Application Priority Data

Apr. 29, 1992 [FR] France .................................. 92/05307
Apr. 28, 1993 [WO] WIPO ...................... PCT/FR93/00412

[51] Int. Cl.⁶ .................. A61M 5/00; A61M 5/14
[52] U.S. Cl. ...................... 604/256; 604/278; 604/280; 128/632
[58] Field of Search ...................... 604/244, 256, 604/257, 258, 278, 264, 280, 167, 164, 165, 171, 284, 283, 275; 128/632, 634, 635, 666, 673, 675

[56] References Cited

U.S. PATENT DOCUMENTS

| 4,701,159 | 10/1987 | Brown et al. ........................ 604/256 |
| 4,781,693 | 11/1988 | Martinez et al. . |
| 4,810,246 | 3/1989 | Frisch et al. . |
| 4,906,232 | 3/1990 | Reynolds ............................ 604/171 |
| 4,913,700 | 4/1990 | Kantrowitz et al. . |
| 4,936,826 | 6/1990 | Amarasinghe . |
| 5,020,543 | 6/1991 | Rothenberg et al. ................. 604/167 |
| 5,022,399 | 6/1991 | Biegeleisen . |
| 5,080,654 | 1/1992 | Picha et al. ......................... 604/167 |
| 5,104,389 | 4/1992 | Deem et al. ......................... 604/167 |
| 5,183,472 | 2/1993 | Jaehrling et al. ................... 604/256 |
| 5,207,656 | 5/1993 | Kranys ................................ 604/167 |
| 5,295,969 | 3/1994 | Fischell et al. ..................... 604/167 |

FOREIGN PATENT DOCUMENTS

| 0266243 | 5/1988 | European Pat. Off. . |
| 9110459 | 7/1991 | WIPO ................................. 604/167 |

*Primary Examiner*—John D. Yasko
*Assistant Examiner*—Ronald K. Stright, Jr.
*Attorney, Agent, or Firm*—Francis A. Sirr; Earl C. Hancock; Holland & Hart llp

[57] ABSTRACT

A sealable external access catheter including a portion implanted in the body of the patient, a fixation or anchoring sleeve extending through the skin, and a portion located outside the patient and provided as its free end with a self-sealing septum made of a material which is repeatably and sealably pierceable by an infusion instrument. The septum may include two fins forming a flat base enabling it to be easily attached to the patient's skin. The catheter is provided with a sealing plug whereby any danger of infection is avoided.

2 Claims, 3 Drawing Sheets

1

EXTERNALIZED SEALED CATHETER WITH LEAKPROOF ACCESS

This is a continuation of application Ser. No. 08/170,206, filed as PCT/FR93/00412, Apr. 28, 1993 published as WO93/21972, Nov. 11, 1993 and now abandoned.

BACKGROUND OF THE INVENTION

1. Field of the Invention

This invention concerns catheters to be implanted inside a patient's body to perform infusion, and more specifically an externalized sealed catheter with leakproof access.

2. Description of Prior Art

Catheters have long existed that can be implanted under a patient's skin, with entry through an access site. The latter is generally in the form of a rigid chamber with a septum just under the patient's skin. To perform a infusion on a patient undergoing periodic chemotherapy, the physician or nurse locates the septum by palpation to insert the infusion needle. The septum is made of material easily penetrated by the infusion needle, but becomes leakproof once again after the needle is withdrawn. Generally, the septum must be replaced after a certain number of infusions, usually several hundred, since it is weakened by the large number of infusions and loses its leakproofness.

Implantation of the septum under the skin may have several disadvantages. Thus, a defect in leakproofness of the septum or displacement of the infusion needle during infusion may cause leakage under the skin. The use of aggressive medication in the infusion product can also be dangerous for the patient because the needle punctures the skin.

There are externalized catheters with one open extremity. They are generally closed by a rigid removable stopper. This stopper is not a septum and cannot be punctured by an infusion needle. At the time of infusion, the stopper is removed and the catheter connected to the source of infusion liquid, using a 'cone luer lock'-type needleless syringe for instance as described in patent EP-A-266.243. Such so-called 'open' systems often result in infection because entry to the catheter is exposed to the air every time infusion is performed.

There are also externalized catheters like that described in patent EP-A-143,518, with the extremity external to the patient closed by a septum. But this septum sealing the catheter is of the pre-existing aperture type so the therapeutic solution can be perfused through a cannula, rather than a needle, as is the case with a self-repairing septum. Unlike the self-repairing septum, this type of septum with a pre-existing aperture cannot be used repeatedly without enlarging the aperture, thereby connecting the catheter with the outside and all the dangers of infection.

SUMMARY OF THE INVENTION

The aim of the invention is thus to produce a leakproof externalized catheter with no danger of infection as can occur with an open externalized catheter.

Another purpose of the invention is to produce an externalized catheter with several lines, one of which contains a control signal transmission support for the infusion performed using another line.

The invention is an externalized catheter, with an internal part that can be implanted inside the patient's body and a part external to the patient through which a needle or other instrument may be inserted to perform an infusion, take a sample or for any other appropriate intervention since the external part is equipped at its free extremity with at least one leakproof stopper made of material that can be punctured repeatedly by the instrument without leakage.

According to another of the invention's characteristics, the catheter may have several lines, with each of the parts external to the patient sealed by a septum that can be punctured by an infusion needle.

BRIEF DESCRIPTION OF THE DRAWINGS

The aims, elements and characteristics of this invention will be better understood through the description below, in reference to the figures, in which:

FIG. 4 shows a catheter with optical fibres and sensors, and FIG. 5 A shows a catheter with two lines, one containing optical fibres for the transmission of signals supplied by a control sensor during infusion while

DESCRIPTION OF THE PREFERRED EMBODIMENTS

Figure 1:
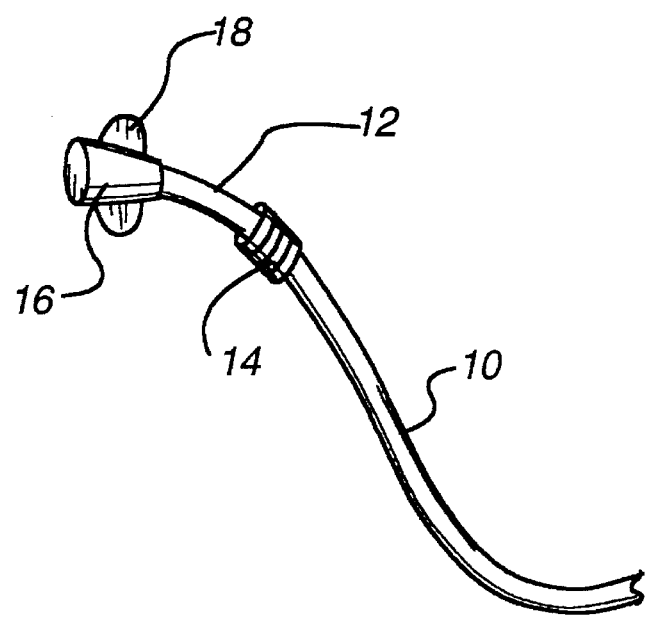
FIG. 1 shows the catheter in this invention with its sleeve tube and septum at the external extremity.

As shown in FIG. 1, the catheter in this invention includes part 10 implanted in the patient's body, generally a blood vessel. The catheter punctures the patient's skin using a fixation sleeve 14 and ends in external part 12. This external part has at its extremity a leakproof stopper 16 with a septum having a self-repairing feature using known material such as silicone through which the infusion needle is inserted to perform infusion of a therapeutic solution to the patient. Stopper 16 is located a few centimetres from sleeve tube 14. It can be detachable, to be replaced and also to adjust the length of external part 12 of the catheter after implantation or facilitate insertion of the catheter for instance in the case of percutaneous intraveinous access route.

As mentioned above, replacement of the self-repairing septum is necessary only after repeated insertion of the infusion needle, up to several hundred times.

For easier fixation on the patient's skin, stopper 16 should have blades 18, forming a flat seat.

Figure 2:
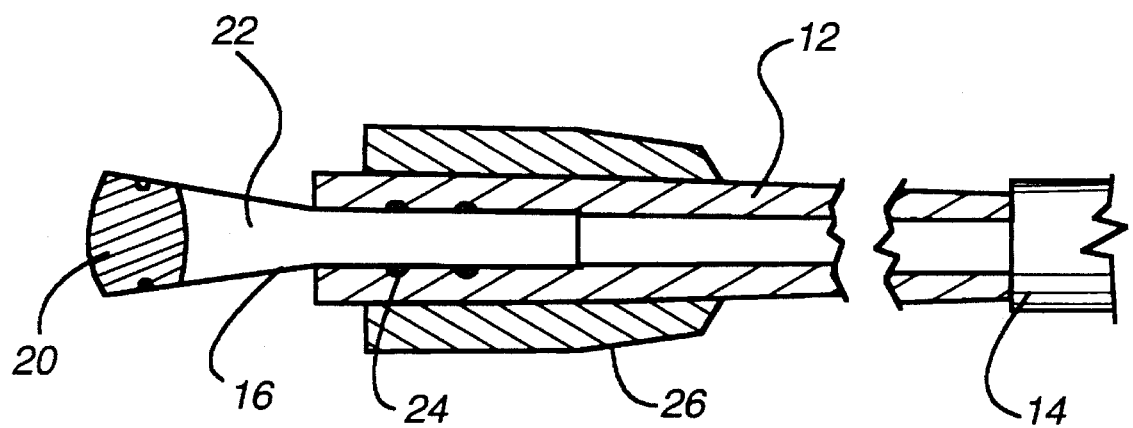
FIG. 2 shows a section of the external extremity of the catheter in this invention.

FIG. 2 shows a section of the extremity of the external part 12 of the catheter. As shown in the figure, stopper 16 is made up of a septum 20 through which the infusion needle is inserted. Septum 20 is prolonged by connecting package 22 acting as a reservoir for the infusion liquid. Two circular threads 24 on stopper 16 help adjust it inside the catheter. Sleeve tube 26 (different from fixation sleeve 14), with a conical profile inside allows package 22 to fit securely inside the catheter, thus ensuring leakproofness of the assembly.

Figure 3:
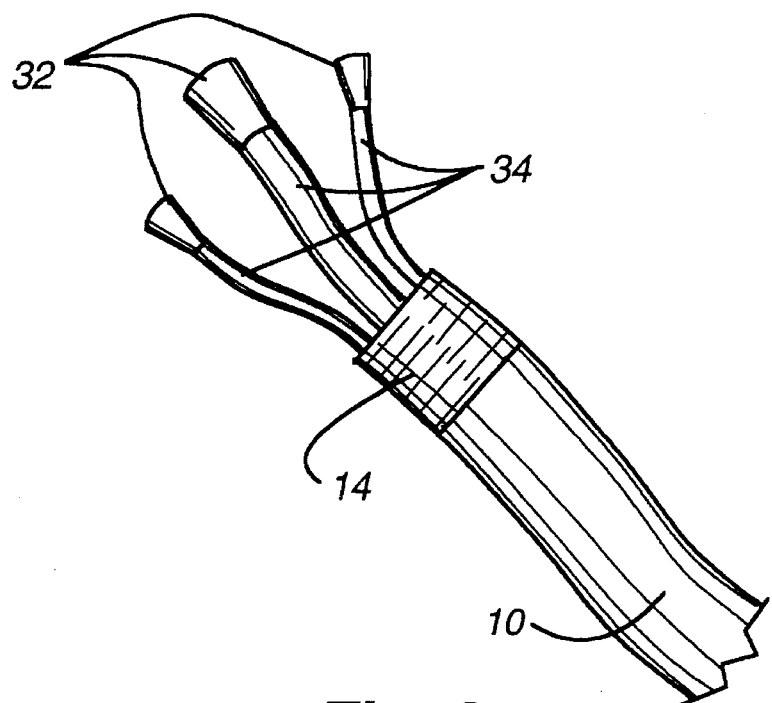
FIG. 3 shows a catheter with several lines.

As shown in FIG. 3, the catheter according to the invention may have several lines or lumina for several independent infusions or interventions. As for the single-line catheter, the catheter in FIG. 3 has one part 10 implanted inside the patient's body. Sleeve tube 14 allows insertion into the patient's skin. The catheter and in particular part 10 with three lines or lumina, the external part has three leakproof stoppers or septum 32 at the extremity of the three external parts 34 prolonging the catheter's three lines. Since the three lines are independent and equivalent to three catheters, their diameters can differ, to be appropriate for infusion or the intervention to be performed through the septum at the extremity of the line. Thus, in FIG. 3, one of the external parts shown has a greater diameter than the other two external parts, and this is obviously true of the corresponding septa as well. It should be noted that the septa corresponding to the various lines can also be located in a single leakproof stopper like stopper 16 shown in FIGS. 1 and 2.

Figure 4:
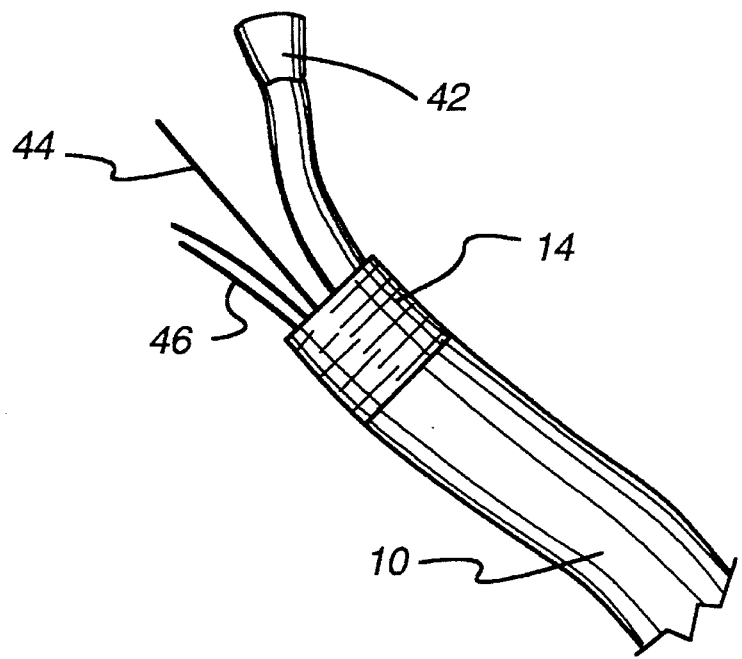

FIG. 4 shows one version of the invention. The catheter in FIG. 4 has an internal part 10 implanted in the patient's body, a sleeve tube 14 for puncturing the skin and its external part 42 with a leakproof stopper or septum at its extremity. But in this form, one of the catheter's lines (or lumina) is used for holding one or more optical fibres 44. The optical fibres 44, that can be removable, make it possible to visualize the patient's vascular condition, thanks to an appropriate visualization device (not shown), to locate thrombosis, or transmit/receive various signals to/from a control device at the catheter's distal extremity. Another line or lumen may be used for holding two wires 46 leading to a sensor at the catheter's other extremity. With an appropriate monitoring device, such a sensor can be used to measure or analyse various physiological constituents such as oxygen in the blood, calcium concentration, etc.

Figure 5A:
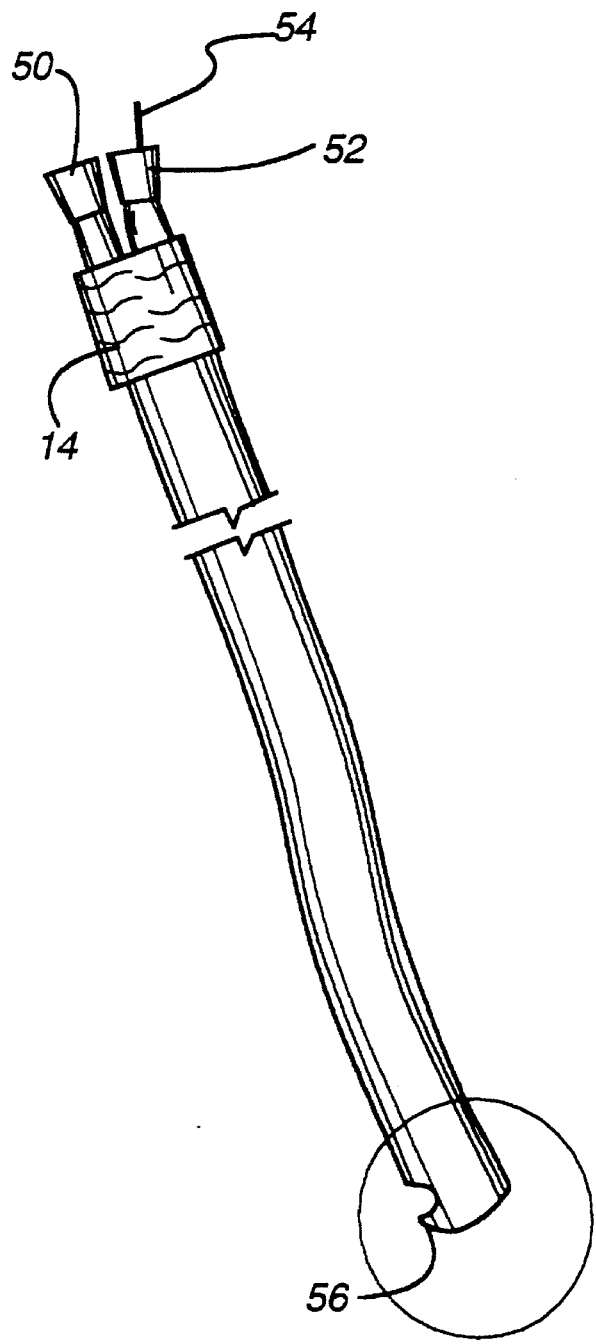
FIG. 5B shows a sectioned and somewhat expanded view of distal extremity 56 of FIG. 5A.
Figure 5B:
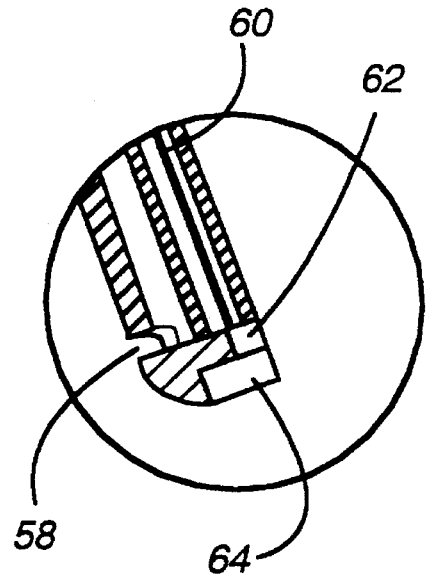

A version with a two-line catheter is shown in FIG. 5A. At its extremity external to the patient, at the output of sleeve tube 14, one of the lines is tipped with a self-repairing septum 50. A second line containing optical fibres is tipped with an nozzle 52 revealing connection 54 of the optical fibres in the line. An enlargement of the section of distal extremity 56 of the catheter is also shown in FIG. 5A. Clearly, the line for injecting the therapeutic solution into the patient's body has an opening 58 to allow the solution to flow. The second line, separated from the first line, contains one or more optical fibres 60 leading directly to a device 62 containing a gallium arsenide-type photovoltaic battery and a miniaturized optical generator, and the device is itself connected to piezoelectric-type sensor 64. The energy supply for device 62 and sensor 64 can thus be provided by lighting the photovoltaic battery thanks to the optical fibres. The signals supplied by sensor 64 are converted into optical signals and transmitted by the optical fibres to the extremity where they are collected and analysed to modify the parameters of infusion, if necessary.

Although a sleeve tube is used in the preferred form of the invention, it is possible to design a catheter without a sleeve tube while remaining within the context of the invention.

It should be noted that when an infusion is performed on a patient, the infusion line is connected to the catheter for some time. Consequently, it is useful to foresee a locking system (not shown in the figures) for connecting the external part of the catheter to the infusion line.

The catheter according to the invention can be used for any infusion, with or without medication, as well as for taking a fluid sample from the human body or to perform any test or other appropriate intervention. It combines the advantages of the implantable access site and externalized catheter without any of its drawbacks. Thus, its leakproof access, even when being connected to an infusion line, minimizes the danger of infection. This advantage is also reinforced by the absence of any intradermal puncture.

Extravasation is unlikely to occur thanks to the easy reliable connection between the catheter and infusion line. Moreover, there is no difficulty in locating and puncturing the septum.

This invention offers many advantages, such as:

the possibility of detecting any leaks appearing at the connection, thereby minimizing danger to the patient, the absence of any intradermal puncture is an advantage for patients who fear injections, possible occlusion of the catheter (thrombosis, precipitation, etc.) can be eliminated by inserting a stylet, mandrel or other appropriate device inside the catheter, through the septum or after removal of the septum, in case of damage, the septum can be replaced without surgery, leaving the catheter in place.

I claim:

1. Catheter apparatus, comprising;

an elongated hollow catheter having a first end, a second end, and an intermediate portion extending between said first and second ends, said first end being adapted to be implanted inside a patient's body, said second end being adapted to be external to the patient's body, a first and a second elongated hollow lumina extending internally through said hollow catheter from said first end to said second end of said catheter, a self-repairing septum mounted to an end of said first lumina that extends from said second end of said catheter, a nozzle mounted to an end of said second lumina that extends from said second end of said catheter, an optical fiber extending through said nozzle and internal of said second lumina from said first end to said second end of said catheter, a photovoltaic battery mounted at said first end of said catheter and in optical communication with said optical fiber so as to be energized by light received from said optical fiber, a piezoelectric sensor mounted at said first end of said catheter and energized by said battery, an optical generator mounted at said first end of said catheter and energized by said battery, and means connecting a signal from said sensor in controlling relation to said optical generator to thereby convert said signal into an optical signal, said optical generator being in optical communication with said optical fiber for transmission of said optical signal to said second end of said catheter.

2. The catheter apparatus of claim 1 including:

a fixation sleeve externally mounted on said intermediate portion of said catheter at a location that is intermediate said first and second ends, said fixation sleeve being adapted for physical engagement with the patient's skin as said first end of said catheter is implanted inside the patient's body and as said second end of said catheter extends external to the patient's body.

\* \* \* \* \*